(12) United States Patent
Phykitt

(10) Patent No.: US 8,580,853 B2
(45) Date of Patent: Nov. 12, 2013

(54) ANALGESIC COMPOSITION AND METHOD OF MAKING THE SAME

(75) Inventor: Howard Phykitt, Rocky Mount, NC (US)

(73) Assignee: Howard Phykitt, Rocky Mount, NC (US)

( * ) Notice: Subject to any disclaimer, the term of this patent is extended or adjusted under 35 U.S.C. 154(b) by 0 days.

(21) Appl. No.: 13/158,544

(22) Filed: Jun. 13, 2011

(65) Prior Publication Data

US 2012/0316140 A1 Dec. 13, 2012

(51) Int. Cl.
*A61K 31/185* (2006.01)

(52) U.S. Cl.
USPC .......... 514/553; 514/576; 514/730; 514/772.2

(58) Field of Classification Search
USPC .................. 514/553, 576, 730, 772.2
See application file for complete search history.

(56) References Cited

U.S. PATENT DOCUMENTS

| | | |
|---|---|---|
| 2,297,599 A | 9/1942 | Wilen |
| 2,985,562 A | 5/1961 | Millard et al. |
| 3,105,792 A | 10/1963 | White |
| 3,495,001 A | 2/1970 | Leonards |
| 3,773,922 A | 11/1973 | Gergely |
| 3,903,255 A | 9/1975 | Gusman et al. |
| 3,985,792 A | 10/1976 | Galat |
| 4,093,710 A | 6/1978 | Sass et al. |
| 4,515,949 A | 5/1985 | Santroch et al. |
| 4,687,662 A | 8/1987 | Schobel |
| 4,704,269 A | 11/1987 | Korab |
| 4,783,551 A | 11/1988 | Galat |
| 4,942,039 A | 7/1990 | Duvall |
| 5,157,030 A | 10/1992 | Galat |
| 5,665,388 A | 9/1997 | Phykitt |
| 5,723,453 A | 3/1998 | Phykitt |
| 5,776,431 A | 7/1998 | Galat |
| 2003/0157029 A1 | 8/2003 | Modi |

FOREIGN PATENT DOCUMENTS

| | | |
|---|---|---|
| EP | 0203768 A2 | 12/1986 |
| FR | 2708853 A1 | 2/1995 |
| GB | 1328591 A | 8/1973 |

*Primary Examiner* — Sreeni Padmanabhan
*Assistant Examiner* — Shobha Kantamneni
(74) *Attorney, Agent, or Firm* — Hultquist, PLLC; Steven J. Hultquist; Mary B. Grant

(57) ABSTRACT

A soluble aspirin composition, comprising: (i) granules including aspirin, heat-treated bicarbonate salt, pharmaceutically-acceptable resin and surfactant, in mixture with: (ii) crystalline particles of pharmaceutically-acceptable acid; and (iii) crystalline particles of heat-treated bicarbonate salt; wherein the soluble aspirin composition when introduced to water undergoes reaction of the crystalline particles of pharmaceutically-acceptable acid with the heat-treated bicarbonate salt and the aspirin to effect effervescing action and disintegration of the granules with conversion of the aspirin to an acetylsalicylate compound of the bicarbonate salt cation so that the composition rapidly dissolves in the water without occurrence of undissolved residue. The composition is solublizable within 30 seconds in cool to cold water to provide an effervescent analgesic solution that can be readily orally administered to an individual in need of analgesia.

21 Claims, No Drawings

ANALGESIC COMPOSITION AND METHOD OF MAKING THE SAME

FIELD

The present disclosure relates to analgesic compositions and methods of making and using the same. More specifically, the disclosure relates to a soluble aspirin analgesic composition having improved dose forms, taste, ease-of-use and aqueous solubility characteristics.

DESCRIPTION OF THE RELATED ART

Approximately 84% of the U.S. population regularly uses non-prescription analgesics for minor pain relief for conditions such as headache, muscle ache or backache. Over $2 billion worth of such analgesics are sold annually by supermarkets, drugstores and mass merchandisers.

The non-prescription analgesics market encompasses pain-relief medications having four principal active chemical ingredients, aspirin, acetaminophen, ibuprofen and naproxen sodium. Brand names are well-established in each of these segments, and include Tylenol (acetaminophen), Advil and Motrin (ibuprofen), Aleve (naproxen sodium), Bayer (aspirin or combination), Excedrin (acetaminophen), Midol and Pamprin (varied formulas for menstrual pain relief).

Aspirin has a number of inherent advantages. Like other pain relievers of the type discussed above, aspirin is effective for treatment of pain, fevers, arthritis, and headaches, but unlike such other analgesic products, aspirin is the only pain reliever shown to reduce the risk of heart attack. In addition, aspirin is the oldest and best established of the common pain relievers, with well over a century of use throughout the world.

In the field of aspirin pain relievers, effervescent soluble aspirin products such as Aspro or Disprin are quite popular in other countries such as Australia, Canada, Great Britain and New Zealand. In the U.S., Alka-Seltzer, an effervescent formulation including aspirin, sodium bicarbonate and citric acid. Alka-Seltzer is the world's number one cure for hangover and is currently sold in over 100 countries, generating annual sales in excess of $100 million. Overall, the soluble aspirin products market worldwide exceeds $2 billion.

The first-generation soluble aspirin products began to appear at the beginning of the last century. See, for example, U.S. Pat. No. 740,703 issued in 1903. These early products were based on various soluble salts, lithium, sodium, potassium, calcium and magnesium as well as with organic amines and amino acids (lysine and ormthine), and were not stable formulations. Their instability resulted from water of crystallization contained in the salts, that resulted in degradation of aspirin into salicylic and acetic acids. Efforts to improve such products focused on removal of the water of crystallization, and formation of anhydrous salts, but the resulting compositions were difficult to handle and expensive to produce, involved unsuitably high levels of metallic elements, and were not economically competitive against aspirin.

Later developments in such first-generation products employed buffering coatings intended to neutralize gastric acidity. Clinical studies showed, however, that is not possible to coat aspirin tablets with sufficient amounts of buffering agent to totally neutralize gastric acid, and such buffering coatings are ineffective in preventing in soluble aspirin particles from adhering to gastrointestinal mucosa. Enteric coatings have been alternatively utilized, but are subject to the same mucosal adhesion problems in the intestinal locus.

Subsequent first-generation soluble aspirin products include products based on soluble salts of aspirin, such as that disclosed in U.S. Pat. No. 3,985,792, in which aspirin is reacted with sodium bicarbonate and water to form a sodium salt solution that then is treated with alcohol and cooled to crystallize sodium acetylsalicylate dihydrate. This dihydrate then is filtered, washed and dehydrated to provide the final product. Such product is, however, extremely susceptible to degradation by moisture, and additionally requires large amounts of alcohol that must be separated by distillation.

The shortcomings of the first generation products were addressed in a second-generation formulation of soluble aspirin developed by the present inventor and more fully described in U.S. Pat. No. 5,723,453. This second-generation product was a stabilized, essentially sodium-free aspirin composition that was readily soluble in aqueous medium. It comprised aspirin granules of predetermined particle size and granular potassium bicarbonate.

Although the soluble aspirin composition of U.S. Pat. No. 5,723,453 achieved improvements over earlier soluble aspirin formulations with respect to taste and dissolution rate, it was nonetheless characterized by some degree of residue and slowed dissolution rate in cold water or other lower temperature aqueous medium, relative to dissolution rate in aqueous media at room temperature ambient conditions.

The art accordingly continues to seek improvement in aspirin compositions, in respect of their dose forms, taste, ease-of-use, dissolution rate and completeness of dissolution in aqueous media.

SUMMARY

The present disclosure relates to a soluble aspirin analgesic composition and methods of making and using same.

In one aspect, the disclosure relates to a soluble aspirin composition, comprising: (i) granules including aspirin, heat-treated bicarbonate salt, pharmaceutically-acceptable resin and surfactant, in mixture with: (ii) crystalline particles of pharmaceutically-acceptable acid; and (iii) crystalline particles of heat-treated bicarbonate salt; wherein the soluble aspirin composition when introduced to water undergoes reaction of the crystalline particles of pharmaceutically-acceptable acid with the heat-treated bicarbonate salt and the aspirin to effect effervescing action and disintegration of the granules with conversion of the aspirin to an acetylsalicylate compound of the bicarbonate salt cation, so that the composition rapidly dissolves in the water without occurrence of undissolved residue.

The disclosure in another aspect relates to a dry solids aspirin composition, comprising: (i) granules including aspirin, heat-treated potassium bicarbonate, pharmaceutically-acceptable resin and surfactant, in mixture with: (ii) crystalline particles of pharmaceutically-acceptable acid; and (iii) crystalline particles of heat-treated potassium bicarbonate.

In a further aspect, the disclosure relates to a method of making a soluble aspirin composition, comprising: agglomerating powdered aspirin and powdered heat-treated bicarbonate salt with a pharmaceutically-acceptable resin and surfactant, to form granules; and mixing the granules with crystalline particles of pharmaceutically-acceptable acid and crystalline particles of heat-treated bicarbonate salt, to yield the soluble aspirin analgesic composition.

The disclosure in a still further aspect relates to a method of providing aspirin treatment to a subject in need thereof, comprising mixing an effective amount of the dry solids aspirin composition of claim 13 with a solubilizing quantity of aqueous medium, to produce a solubilized aspirin solution, and administering said solubilized aspirin solution to said subject.

As used herein, the term "bicarbonate salt" refers to a pharmaceutically acceptable salt compound including a bicarbonate anion. The cationic component of the salt compound may for example comprise one or more of potassium, sodium, calcium, magnesium, lithium, or any other suitable cation species. A preferred bicarbonate salt in the compositions, dose forms, and methods of the disclosure is potassium bicarbonate. While the disclosure hereinafter is primarily directed to potassium bicarbonate as an exemplary bicarbonate salt, it will be recognized that the disclosure is not thus limited, but rather is intended to be broadly construed and to encompass any pharmaceutically acceptable bicarbonate compounds having useful cationic moieties in the compositions, dose forms and methods of the disclosure.

As used herein, the term "heat-treated" in reference to the bicarbonate salt refers to a bicarbonate salt that has been subjected to elevated temperature sufficiently long enough to impart to it a pH in a range of from 8.4 to 10.0. Such heat treatment involves at least partial conversion of the bicarbonate to a carbonate. Specific pH ranges in various embodiments of the disclosure can include pH in a range of from 8.5 to 9.7, more preferably a pH in a range of from 8.9 to 9.6, and most preferably a pH of about 9.5. In various applications, the heat-treated bicarbonate salt may have a pH in a range with a lower end point that in various embodiments may be 8.5, 8.6, 8.7, 8.8, or 8.9, and with an upper end point that in various embodiments may be 9.1, 9.2, 9.3, 9.4, 9.5, 9.6, 9.7, 9.8 or 9.9, it being appreciated that any of such single lower point values and single upper point values may in such various embodiments delimit specific ranges of pH within which the disclosure may be practiced.

As used herein, the term "water-soluble" refers to aqueous solubility, and encompasses the solubility categories of "very soluble," "freely-soluble," "soluble" and "sparingly soluble," as described in Remington's Pharmaceutical Sciences and Remington: Practice of Pharmacy.

Other aspects, features and embodiments of the disclosure will be more fully apparent from the ensuing description and appended claims.

DETAILED DESCRIPTION

The present disclosure relates to an analgesic composition and methods of making and using the same, having aspirin as an active ingredient, in a form having appealing taste, ease-of-use, dissolution rate and completeness of dissolution in aqueous media.

The present disclosure is based on the discovery that an extremely quick and residue-free dissolution of aspirin can be effected, when the aspirin is incorporated in granules containing powdered heat-treated bicarbonate salt, pharmaceutically-acceptable resin, and surfactant, with such aspirin-containing granules being provided in mixture with crystalline particles of pharmaceutically-acceptable acid and crystalline particles of heat-treated bicarbonate salt. In such composition containing aspirin-incorporating granules and free crystalline particles of acid and bicarbonate salt, the free acid crystals react with the free bicarbonate salt crystals to establish an intense initial effervescence, while at the same time, the free acid crystals react with bicarbonate salt in the granules, to likewise produce an intensive reaction that causes the granules to rapidly fragment and expose new surface containing the bicarbonate salt, which thereupon intensively reacts with the acid crystals to effect further fragmentation and disintegration of the granule fragments. The reaction involves the formation of potassium acetylsalicylate from the aspirin in the granules, with the potassium acetylsalicylate immediately dissolving in the aqueous medium without residue being formed.

The granules thus include aspirin, powdered heat-treated bicarbonate salt, resin and surfactant. Such granules by themselves are susceptible to dissolution in the aqueous medium to which the granules are introduced, but the presence of the free crystals of pharmaceutically-acceptable acid and free crystals of heat-treated bicarbonate salt greatly accelerate the reaction of the powdered heat-treated bicarbonate salt and aspirin in the granules so that extremely rapid dissolution of all ingredients of the composition is achieved, e.g., in less than 60 seconds, without residue formation.

The composition of the present disclosure thus comprises aspirin-containing and heat-treated bicarbonate salt-containing granules, in mixture with crystals of a pharmaceutically-acceptable acid and crystals of heat-treated bicarbonate salt. The composition may be formulated with any suitable relative amounts and proportions of the various ingredients in relation to one another, as effective to provide dissolution the composition in aqueous medium within 60 seconds without residue formation, and as effective to provide aspirin treatment to a subject, e.g., a human subject or a non-human mammalian subject, upon drinking or other administration of such aqueous medium containing the dissolved composition of the disclosure.

In one aspect, the disclosure relates to a soluble aspirin composition, comprising: (i) granules including aspirin, heat-treated bicarbonate salt, pharmaceutically-acceptable resin and surfactant, in mixture with: (ii) crystalline particles of pharmaceutically-acceptable acid; and (iii) crystalline particles of heat-treated bicarbonate salt; wherein the soluble aspirin composition when introduced to water undergoes reaction of the crystalline particles of pharmaceutically-acceptable acid with the heat-treated bicarbonate salt and the aspirin to effect effervescing action and disintegration of the granules with conversion of the aspirin to an acetylsalicylate compound of the bicarbonate salt cation, so that the composition rapidly dissolves in the water without occurrence of undissolved residue.

Such soluble aspirin composition can be formulated in which the bicarbonate salt comprises one or more of potassium bicarbonate, sodium bicarbonate, calcium bicarbonate, magnesium carbonate and lithium carbonate.

Aspirin may be present in such composition at a concentration of from 50 to 2000 mg. The composition can be formulated so that the heat-treated bicarbonate salt comprises heat-treated potassium bicarbonate having a pH in a range of from 8.4 to 10. In the compositions of the disclosure, the pharmaceutically-acceptable resin can be selected from the group consisting of polyvinyl pyrollidone, polyvinyl alcohol, acrylic acid polymers, methacrylic acid polymers, sulfonated styrenes, sulfonated dimethyl benzenes, modified celluloses, and dextrans. In various embodiments, the pharmaceutically-acceptable resin comprises polyvinyl pyrollidone.

The pharmaceutically-acceptable resin in various compositions of the disclosure can have a concentration in a range of from about 1.5 to about 4 percent by weight, based on total weight of the granules. The pharmaceutically-acceptable acid in the compositions of the disclosure can be of any suitable type, and can for example be selected from the group consisting of citric acid, acetic acid, adipic acid, benzoate acid, caproic acid, malic acid, malonic acid, nicotinic acid, lauric acid, glycolic acid, oxalic acid, phosphoric acid, succinic acid, oleic acid, palmitic acid, proprionic acid, cinnamic acid, gluconic acid, stearate acid, and tartaric acid.

The surfactant in the compositions of the disclosure can be of any suitable type and can for example be selected from the group consisting of sodium laurel sulfate, polyoxyethylene sorbitan monolaurate, polyoxyethylene sorbitan monooleate, polyethylene glycol 300, propoxylated polyethylene glycol, polyoxyethylene lauryl ether, and diethylene glycol monoethyl ether. In one embodiment, the surfactant comprises sodium laurel sulfate at a concentration in a range of from 0.01 to 0.1 weight percent, based on total weight of the granules.

Various compositions of the disclosure can be constituted to include at least one ingredient selected from the group consisting of flavorants, sweeteners, acetaminophen (paracetamol), and caffeine. The compositions of the disclosure can be formulated in various embodiments to be oil-free in character, and to have a moisture content less than 0.5% by weight, based on total weight of the composition.

Another aspect of the disclosure relates to a dry solids aspirin composition, comprising: (i) granules including aspirin, heat-treated potassium bicarbonate, pharmaceutically-acceptable resin and surfactant, in mixture with: (ii) crystalline particles of pharmaceutically-acceptable acid; and (iii) crystalline particles of heat-treated potassium bicarbonate.

Such dry solids aspirin composition may be formulated to include aspirin at a concentration of from 50 to 2000 mg. In specific embodiments, pH of the heat-treated potassium bicarbonate can be in a range of from 8.4 to 10. The pharmaceutically-acceptable resin in various embodiments can comprise polyvinyl pyrollidone. The pharmaceutically-acceptable resin can have any suitable concentration, e.g., a concentration in a range of from about 1.5 to about 4 percent by weight, based on total weight of the granules. The pharmaceutically-acceptable acid can be of any suitable type in the dry solids aspirin composition, and can for example be citric acid, wherein the surfactant in the composition comprises sodium laurel sulfate.

The dry solids aspirin composition can be formulated to include at least one ingredient selected from the group consisting of flavorants, sweeteners, acetaminophen and caffeine. In a specific implementation, the dry solids aspirin composition is oil-free in character, and has moisture content less than 0.5% by weight, based on total weight of the composition.

The disclosure in another aspect contemplates a method of making a soluble aspirin composition, comprising: agglomerating powdered aspirin and powdered heat-treated bicarbonate salt with a pharmaceutically-acceptable resin and surfactant, to form granules; and mixing the granules with crystalline particles of pharmaceutically-acceptable acid and crystalline particles of heat-treated bicarbonate salt, to yield the soluble aspirin analgesic composition.

A further aspect of the disclosure relates to a method of providing aspirin treatment to a subject in need thereof, comprising mixing an effective amount of the dry solids aspirin composition of claim 13 with a solubilizing quantity of aqueous medium, to produce a solubilized aspirin solution, and administering said solubilized aspirin solution to said subject. In such method, the aqueous medium may comprise water or other aqueous liquid. The method of aspirin treatment can be conducted to provide treatment of one or more of headache, migraine, rheumatic pains, neuralgia, menstrual pain, toothache, and symptoms of colds and influenza.

Thus, the soluble aspirin composition of the disclosure in various embodiments includes powdered aspirin and powdered heat-treated bicarbonate salt, agglomerated together with a pharmaceutically-acceptable resin and surfactant, to constitute granules. The granules can be used to formulate dry solids dose forms, as a mixture of the granules with crystalline particles of pharmaceutically-acceptable acid and crystalline particles of heat-treated bicarbonate salt.

In one preferred embodiment, the bicarbonate salt in the granules and in the crystalline particles is potassium bicarbonate. It will be appreciated that the bicarbonate salt in the granules and in the crystalline particles may be the same as, or alternatively different from, one another.

The composition of the disclosure thus can be provided in the form of a dry solids mixture, as a dose form that is readily soluble in an aqueous medium, e.g., water or a water-containing liquid medium.

The dry solids analgesic dose form of the disclosure can be formulated to provide any suitable concentration of the aspirin active ingredient, e.g., a concentration of from 50 mg to 2000mg. In various embodiments, the aspirin active ingredient may be present in an amount, measured in milligrams, in a range with a lower end point of 80, 100, 200, 250, 300, 400, 500 or 600, and with an upper end point that in various embodiments may be 700, 800, 1000, 1200, 1400, 1500, 1600, or 1800, it being appreciated that any of such single lower point values and single upper point values may in such various embodiments delimit specific ranges of aspirin concentration within which the disclosure may be practiced. In one embodiment, the composition contains aspirin in an amount of 81 mg.

The aspirin used in the composition of the disclosure may have any suitable particle size and particle size distribution. The aspirin may for example have a mesh size in a range of from 8 to 350 mesh. In various embodiments, the aspirin ingredient may have a mesh size in a range with a lower end point of 10, 20, 30, 50, 75, 100, 125, 150, 175, 200, 250 or 300, and with an upper end point that in various embodiments may be 310, 315, 320, 325, 330, 335, 340 or 345, it being appreciated that any of such single lower point values and single upper point values may in such various embodiments delimit specific ranges of aspirin mesh size within which the disclosure may be practiced.

The compositions of the disclosure thus employ heat-treated bicarbonate salt in two distinct forms, viz., in a granular form (in granules including powdered heat-treated bicarbonate salt, e.g., potassium bicarbonate, together with powdered aspirin, resin and surfactant ingredients) and in a crystalline particle form. The heat-treated bicarbonate salt in granular form can have any suitable particle size and size distribution characteristics. For example, in various specific embodiments, the heat-treated bicarbonate salt in the granules may have a mesh size in a range of from 10 to 325 mesh, while heat-treated bicarbonate salt in crystalline particle form may have a mesh size in a range of from 8 to 350 mesh, a range of from 10 to 150 mesh, a range of from 20 to 100 mesh, or any other suitable mesh size range.

In various embodiments, the heat-treated bicarbonate salt ingredient in the respective granules and crystalline particles may have a mesh size in a range with a lower end point of 12, 20, 30, 50, 75, 100, 125, 150, 175, or 180, and an upper end point that in various embodiments may be 200, 210, 220, 230, 250, 280, 300, 320, 330 or 350, it being appreciated that any of such single lower point values and compatible single upper point values may in various embodiments delimit specific ranges of heat-treated bicarbonate salt mesh size within which the disclosure may be practiced. In general, the bicarbonate salt may be widely varied in composition in relation to the aspirin component. For example, in various embodiments, the ratio of the bicarbonate salt to aspirin may be in a range of from about equimolar amounts of each of such ingredients up to a ratio value of 4 or more.

The pharmaceutically-acceptable resin utilized in soluble aspirin compositions of the present disclosure may be of any suitable pharmaceutically-acceptable type, and may for example be selected from among polyvinyl pyrollidone, polyvinyl alcohol, acrylic acid polymers, methacrylic acid polymers, sulfonated styrenes, sulfonated dimethyl benzenes, cellulosic, and modified cellulosic polymers (e.g., hydroxypropylmethyl cellulose). Polyvinyl pyrollidone is a preferred resin. The resin utilized in the composition may be present in specific embodiments of the formulation at any suitable concentration. In various embodiments, concentration of the resin may be in a range of from about 1.5 to about 4 percent by weight, and more preferably from about 1.8 to about 3 percent by weight, based on total weight of the granules (aspirin, bicarbonate salt, resin and surfactant ingredients).

In other embodiments, the pharmaceutically-acceptable resin may have a concentration in a range with a lower end point that in such embodiments may be 1.6%, 1.65%, 1.7%, 1.75%, or 1.8%, and with an upper end point of 2.1%, 2.2%, 2.5%, 2.8%, 3.0%, 3.25%, 3.5%, 3.75%, or 3.8%, by weight, based on total weight of the granules.

In general, the amount of the pharmaceutically-acceptable resin is such that it is effective to effect agglomeration of the granules of powdered aspirin and powdered heat-treated bicarbonate salt, e.g., potassium bicarbonate. Accordingly, the amount of resin in a specific embodiment may vary depending on the type of resin employed, the type of surfactant employed, and the agglomerative character of the powdered heat-treated bicarbonate salt and powdered aspirin that are present in the granules.

The pharmaceutically-acceptable acid employed in compositions of the present disclosure likewise may be of any suitable type, and in specific embodiments can include one or more acids such as citric acid, acetic acid, adipic acid, benzoate acid, caproic acid, malic acid, malonic acid, nicotinic acid, lauric acid, glycolic acid, oxalic acid, phosphoric acid, succinic acid, oleic acid, palmitic acid, proprionic acid, cinnamic acid, gluconic acid, stearate acid, tartaric acid. Additional pharmaceutically-acceptable acids potentially useful in the compositions of the present disclosure are described in P. H. Stall and C. G. Wermuth, editors, Handbook of Pharmaceutical Salts: Properties, Selection and Use, Weinheim/Zurich: Wiley-VCH/VHCA, 2002. Citric acid is a preferred acid for such purpose, with citric acid anhydrous USP being most preferred. The anhydrous citric acid in one embodiment is pre-dried to low moisture content, e.g., less than 0.01% moisture content.

In general, the pharmaceutically-acceptable acid can be of any suitable type that is reactive with the heat-treated bicarbonate salt in the composition. Such acid is advantageously present in solid crystal form, as crystalline particulate material, with large size acid crystals being useful in effecting break-up of the surface foam that would otherwise be present, by forming gas bubbles in the reaction, which act to break up surface foam.

The specific amount of pharmaceutically-acceptable acid employed in compositions of the present disclosure is desirably selected to effect reaction with the crystalline particles of heat-treated bicarbonate salt present in the composition, to effect effervescing action in aqueous medium that in turn assists in the break-up of the granules containing powdered heat-treated bicarbonate salt and powdered aspirin, and further reaction of the heat-treated bicarbonate salt that is present in the granules.

The pharmaceutically-acceptable acid may have any suitable mesh size, e.g., a mesh size in a range of 4-325 mesh, with a mesh size in a range of 5-100 mesh being preferred, a mesh size in a range of 5-40 mesh being more preferred, a mesh size in a range of 8-30 mesh being still more preferred, and a mesh size in a range of from 8 to 14 mesh being most preferred. The mesh size of the pharmaceutically-acceptable acid may be in a mesh size range that in various embodiments has a lower end point of 5, 5.5, 6, 6.5, 7, or 7.5 mesh, and an upper end point that in various embodiments may be 35, 40, 45, 50, 60, 75, 80, 100, 120, 140, 150, 160, 175, 180, 200, 220, 250, 280, 290 or 310 mesh, it being appreciated that any of such single lower point values and compatible upper single point values may be in various embodiments delimit specific ranges of pharmaceutically-acceptable acid within which the disclosure may be practiced.

Surfactants useful in the compositions of the present disclosure include pharmaceutically-acceptable surface active agents that are compatible with the other ingredients of the analgesic composition, and include sodium laurel sulfate, polyoxyethylene sorbitan monolaurate, polyoxyethylene sorbitan monooleate, polyethylene glycol 300, propoxylated polyethylene glycol, polyoxyethylene lauryl ether, and diethylene glycol monoethyl ether. Sodium laurel sulfate is a preferred surfactant species.

The surfactant may be employed in any suitable amount that is effective for good dissolution and effervescing action of the composition. While any suitable amount of surfactant may be employed, it has been found advantageous in various embodiments of the disclosure to utilize surfactants in a concentration that is less than 0.1% by weight, based on total weight of the granules. The surfactant in specific embodiments may have a concentration in a range of from 0.01 to 0.1 weight percent, based on total weight of the granules. In various embodiments, the surfactant may have a concentration in a range with a lower end point of 0.011, 0.012, 0.013, 0.014, 0.015, 0.020, 0.030, 0.040 or 0.045 weight percent, based on total weight of the granules, and an upper end point that in various embodiments may be 0.050, 0.060, 0.070, 0.080, 0.090 or 0.095 weight percent, based on total weight of the granules. It will also be appreciated that any of such single lower point values and compatible single upper point values may in various embodiments delimit specific ranges of surfactant concentration within which the disclosure may be practiced.

In various specific embodiments, the amount of the surfactant based on the total weight of the soluble aspirin composition may be on the order of about 0.05 weight percent or less, based on total weight of the composition, e.g., in a range of from about 0.005 weight percent to about 0.05 weight percent.

The resin and surfactant preferably are dissolved in a pharmaceutically-acceptable solvent and then combined with the powdered aspirin and powdered heat-treated bicarbonate salt ingredients in a high or low shear granulator or a fluid bed granulator. The solvent can be of any suitable type, e.g., and may include one or more solvent species selected from among alcohols, ethers, glycols, glycol ethers, N,N-dimethylacetamide (DMA), dimethyl sulfoxide (DMSO), glycerol, 1,2,-propylene-diol (PG), and polyethylene glycols. Preferred solvents include alcohols, with isopropyl alcohol being most preferred. In general, the amount of solvent employed is minimized, as the amount necessary to dissolve the resin and surfactant ingredients of the composition and provide a resulting solution amenable to combination with the powdered aspirin and powdered bicarbonate salt ingredients, for the purpose of effecting granulation.

Compositions of the disclosure, in addition to the aspirin, bicarbonate salt, pharmaceutically-acceptable acid, pharmaceutically-acceptable resin and surfactant ingredients, can comprise additional active ingredients, flavorants, solubilizers, stabilizers, anti-oxidants, and/or other excipients. For example, the composition may contain a vasomodulator, such as a methylxanthine, e.g., caffeine, or other active ingredient(s), e.g., acetaminophen, and/or flavorants, sweeteners and similar ingredients, e.g., Sucralose™ sweetener, Aspartame™ sweetener, vanillin, etc. Flavorants are preferably spray-dried or otherwise pre-dried to less than 0.5% moisture content. The flavor ingredients are advantageously oil-free in character, to provide high rate solubilization of the composition in aqueous medium, without the occurrence of a surface layer of undissolved particulate components or other residue after the dry solids analgesic composition has been added to water or other aqueous medium.

Specific flavor ingredients include flavorants commercially available from Givauden S.A. (Vernier, Switzerland) under the trademarks TasteEssentials™, TasteSolutions™, ByNature™, and PureDelivery™. In one embodiment, the flavorants are blended with Sucralose™ and vanillin crystals. In other embodiments, flavors can be varied by different granulations of suitable flavors, such as fruit flavors (peach, cherry, etc.).

In one embodiment, the soluble aspirin analgesic composition of the disclosure comprises substantially equal amounts of aspirin and acetaminophen, and optionally caffeine. For example, an illustrative composition of such type may contain 325 mg of the soluble aspirin, and 325 mg of acetaminophen powder. More generally, aspirin and acetaminophen may be present in the composition in any suitable amounts or ratios in relation to one another. In a specific embodiment, each of the aspirin and acetaminophen ingredients is present in an amount that is within a range of from 50 mg to 500 mg. In another specific embodiment, each of the aspirin and acetaminophen ingredients is present in an amount of 81 mg.

The compositions of the disclosure preferably are in a substantially anhydrous state, as a dry solid particulate material, e.g., having a water/moisture content less than 0.5% by weight, based on the weight of the composition, more preferably less than 0.3% by weight, and most preferably less than 0.1% by weight, on the same composition weight basis. The composition also is advantageously completely oil-free in character, to maximize compatibility of the composition with water or other aqueous medium.

The soluble aspirin analgesic composition of the disclosure may be formulated in any suitable manner producing the granules of powdered aspirin and powdered heat-treated bicarbonate salt, in mixture with crystalline particles of pharmaceutically-acceptable acid and crystalline particles of heat-treated bicarbonate salt.

The crystalline particles of heat-treated bicarbonate salt may be provided in any appropriate amount in relation to the powdered bicarbonate salt that is in the granules of the composition. Specific relative proportions may be readily determined for use without undue experimentation, within the skill of the art, based on the disclosure herein. In various specific embodiments, the amount of the crystalline particle heat-treated bicarbonate salt can be in a range of from 0.1 to 5.0 times the amount of powdered heat-treated bicarbonate salt in the granules of the composition. More typically, the amount of the heat-treated bicarbonate salt in the crystalline particles in the composition is in a range of from 0.25 to 0.75 times the amount of the heat-treated bicarbonate salt in the granules of the composition.

In one embodiment, the composition of the disclosure includes 650 milligrams powdered aspirin and 750 milligrams powdered heat-treated potassium bicarbonate in the granules of the composition, in mixture with 300 milligrams of heat-treated crystalline particles of potassium bicarbonate, and 300 milligrams of anhydrous crystalline particles of citric acid. In such embodiment, the granules are formed using polyvinylpyrollidone and sodium laurel sulfate in isopropanol, and the composition further contains 80 milligrams of sweetener and flavor ingredients.

In such illustrative composition, the heat-treated potassium bicarbonate in particulate crystalline form can have a mesh size in a range of from 20 to 60 mesh. The heat-treated powdered potassium bicarbonate in the granules can have a mesh size on the order of 200 mesh, and the powdered aspirin in the granules can have a mesh size on the order of 325 mesh. Such illustrative composition is oil-free and dry, having a moisture content of less than 0.5% moisture by weight, based on weight of the composition.

The method of making the soluble aspirin analgesic composition of the disclosure, in one embodiment thereof, includes the steps of: agglomerating powdered aspirin and powdered heat-treated bicarbonate salt with a pharmaceutically-acceptable resin and surfactant, to form granular solids; and mixing the granular solids with crystalline particles of pharmaceutically-acceptable acid and crystalline particles of heat-treated bicarbonate salt, to yield the soluble aspirin analgesic composition.

The soluble aspirin analgesic composition of the disclosure is advantageously provided as a dry solids mixture that is readily soluble in aqueous medium such as water. The composition may for example be packaged in a packet, bag, vial or other container, to which water or other aqueous medium may be added, to provide an effervescent analgesic solution that is orally administerable to a subject (e.g., human, dog, cat, or other animal) in need of analgesia.

The soluble aspirin analgesic compositions of the disclosure are highly stable in character, quickly dissolve in water or other aqueous medium, and leave no or negligible residue. The effervescent analgesic solution that is produced by mixing the analgesic composition with an aqueous medium, is highly effective in producing analgesia.

The composition of the disclosure, in one embodiment thereof, includes the following ingredients: potassium bicarbonate, USP granular; potassium bicarbonate, USP milled; aspirin, USP milled; sweetener; spray dried flavors; citric acid anhydrous, USP; flavoring; surfactant; pharmaceutically-acceptable carrier resin; alcohol; acetaminophen; and, optionally, caffeine.

These ingredients in raw material form may be pretreated by drying to achieve a moisture content of less than 0.5%, if the material is not already dried to such extent. All solid ingredients are delumped and screened. Potassium bicarbonate materials starting materials are heat treated, e.g., to raise pH level thereof to suitable level in a pH range of from 8.4 to 10, e.g., a pH value in a range of 8.5 to 9.7, more preferably a pH value in a range of 8.9 to 9.6, and most preferably a pH value in the vicinity of pH 9.5. The carrier resin and surfactant are dissolved in a minimum amount of solvent so that the resulting composition can be combined with the powdered heat-treated bicarbonate salt and powdered aspirin to form the granules.

The heat treating, blending, packaging and other processing steps may be carried out with appropriate machinery within the skill the art, based on the disclosure herein. In one embodiment, such machinery may include a twin cone vacuum rotating dryer equipped with a heating jacket, a granulator, a vacuum pump drier, a solids mill, a pH monitoring device, as well as sealable storage containers, and a supply of steam or hot oil.

In the granulation operation, a high shear granulator/vacuum dryer is preferably used. Other options include use of a high or low shear granulator in combination with a closed circuit fluid bed dryer with solvent recovery capability or vacuum drying with solvent recovery. A peristaltic pump liquid binder delivery system can be employed, with a binder mixing tank and agitator. Blending operations may be carried out with a slant cone blender or other appropriate blending machine. High shear mixing may be conducted with appropriate high shear mixers in milling and other mixing operations.

The ingredients of the soluble aspirin composition of the disclosure are advantageously processed so that the constituent particles therein are non-floating in character, when the dry solids composition is mixed with water or other aqueous medium.

Packaging may be carried out with vertical form/fill/seal stick packaging machines equipped with an inert gas purge, and conventional box packaging and case packaging equipment may be employed.

In the granulation process, heat-treated bicarbonate salt, aspirin and optionally caffeine may be processed in a high shear mixer. Such ingredients may be sized to avoid breaking any of the granules down to powder. The carrier resin and surfactant are dissolved in a predetermined minimum amount of the pharmaceutically-acceptable solvent to form a binder solution. With the choppers and mixing blade of the granulator set at appropriate speed, the binder solution is added and granulation is continued until a desired small particle size and high density of granules is achieved. When granulation is completed, heat and vacuum are applied to dry the granulated mixture to a suitably low moisture content, e.g., a moisture content in a range of from 0.05% to 0.5% moisture content. The granulated mixture then is milled to a suitable particle size, e.g., in a range of from 12 to 100 mesh, more preferably in a range of 25 to 75 mesh.

In the manufacturing operation, the granules are kept small and dust free. This is important in providing effective solubilization character of the final product. Excessively large granules will float to the surface of the aqueous dissolution medium and take longer to dissolve, leaving undissolved particles on the side of the container of the aqueous medium. An excessively small granule size will not achieve a desired mixture of all granulated ingredients, and will not dissolve properly (i.e., undissolved ingredients will be left as a residue). The particular size of the granules containing the heat-treated bicarbonate salt, aspirin, resin and surfactant can be readily empirically determined without undue effort for a given application of the disclosure, within the skill of the art, based on the disclosure herein.

Flavor, sweetener and pharmaceutically-acceptable acid ingredients are delumped and preblended together to form a preblended mixture before final blending. In final blending, the granulated mixture, containing the aspirin and heat-treated bicarbonate salt, is mixed with the preblended mixture and heat-treated crystalline particles of bicarbonate salt, and optionally additional heat-treated granular bicarbonate salt. The resulting blended product then is packaged for subsequent use. Packaging may for example be carried out under nitrogen purging, with the product being introduced into sealed stick packs.

The soluble aspirin composition of the disclosure comprises a granulated portion of aspirin and bicarbonate salt, in a finely granulated form, and a blended portion of pharmaceutically-acceptable acid crystals and heat-treated bicarbonate salt crystals, which react immediately when exposed to water, thereby breaking down the granules in the composition. Such composition thus includes granules containing heat-treated bicarbonate salt, as well as free-form crystalline particles of heat-treated bicarbonate salt.

The compositions of the disclosure can contain any suitable dosage of aspirin, as desired for specific treatment of subjects in need of analgesia. In one embodiment, the amount of aspirin is in a range of from 500 to 600 milligrams, in a 2 gram dose form (dry solids) suitable for quick dissolution in aqueous medium.

The amount of surfactant utilized in the compositions of the present disclosure is extremely low in comparison to other soluble aspirin formulations of the prior art. In compositions of the present disclosure, the amount of surfactant typically is below 0.10% by weight, based on total weight (dry solids weight) of the granules in the soluble aspirin composition, and may be as low as 0.016 to 0.018 weight percent, or lower, on the same dry solids weight basis.

In another illustrative embodiment, the soluble aspirin composition of the disclosure contains 650 milligrams aspirin, 350 milligrams citric acid in large crystal form, 1,000 milligrams of heat-treated potassium bicarbonate, Sucralose™ sweetener, vanillin and flavor ingredients.

The soluble aspirin composition of the disclosure is an effervescing, bicarbonate salt-based solubilizable aspirin that typically dissolves in water or other aqueous medium in less than 30 seconds, to constitute a ready-to-drink dose. The dry solids composition in use is added to an appropriate amount of water or other aqueous medium, e.g., 2 or more ounces of cold water. Warm water may also be employed, and the rate of dissolution of the dry solids composition of the disclosure increases with increasing temperature of the aqueous medium. When water is combined with the composition, a chemical reaction takes place involving reaction of the aspirin, bicarbonate salt, and pharmaceutically-acceptable acid ingredients. This reaction converts the ingredients into an acetylsalicylate compound of the bicarbonate salt cation (e.g., potassium acetylsalicylate in the case of potassium bicarbonate as the bicarbonate salt), and the acetylsalicylate compound immediately dissolves in water, leaving little or no undissolved residue.

The soluble aspirin composition of the present disclosure achieves a substantial advance over the soluble aspirin composition of my U.S. Pat. No. 5,723,453, in respect of taste, rate and extent of dissolution, and ease of use characteristics. Whereas a composition of my prior patent may require 10 minutes to achieve near-complete dissolution, with residual undissolved particles remaining at the surface of the aqueous medium and significant residue at the bottom of the liquid volume, compositions of the present disclosure typically dissolve without stirring or agitation, in less than 60 seconds, e.g., in 30 seconds or less, with high rate reaction effecting dissolution in as little as one ounce of water for the aforementioned 2 gram dose of the dry solids composition, and with no residue or floating solids. The resulting soluble aspirin aqueous formulation is characterized by an absence of powder solids.

The soluble aspirin composition of the present disclosure is formulated so that all aspirin is bound to particles of bicarbonate, i.e., the composition contains no non-agglomerated aspirin. The granules, containing aspirin, powdered heat-treated bicarbonate salt, resin and surfactant, are in mixture with crystalline particles of pharmaceutically-acceptable acid, such as citric acid, and crystalline particles of heat-treated bicarbonate salt, e.g., potassium bicarbonate. When the soluble aspirin composition is introduced to water or other aqueous medium, the pharmaceutically acceptable acid crystals and the heat-treated bicarbonate salt crystals strongly react with one another to effect effervescence and mixing of the composition in the liquid volume, and the pharmaceutically acceptable acid crystals react with the heat-treated bicarbonate salt in the granules to reactively break up and disperse the granules, with the reaction involving the aspirin in the granules, to yield potassium acetylsalicylate, which immediately dissolves in the aqueous medium without residue.

The granules (containing aspirin, powdered heat-treated bicarbonate salt, resin and surfactant) by themselves would dissolve in the aqueous medium to which the granules are introduced, but the presence of the acid crystals and bicarbonate salt crystals greatly accelerate and enhance such dissolution so that the granules undergo reactive fragmentation, exposing more granule surface, which then reacts to effect further fragmentation and breakup of the initial granule fragments, etc., so that an extremely rapid dissolution of the aspirin is effected.

The soluble aspirin compositions of the present disclosure achieve a significant advance in the art, in that complete dissolution of the solid particulate composition is achieved in less than 60 seconds with no residue. Further, in contrast to the formulations of Galat U.S. Pat. No. 5,107,030, which require substantial change of pH in aqueous medium to effect any dissolution whatsoever, the compositions of the present disclosure are dissolved without significant change of pH. Further, the formulations of the Galat patent have been rigorously evaluated and tested by the present inventor for a period in excess of six months, without success in reproducing the results stated in such patent. Specifically, the present inventor was unable to effect any substantial degree of dissolution by the teachings of such patent, without addition of excessive amounts of surfactant and alteration of pH.

The soluble aspirin composition of the present disclosure has application to the treatment of headache, migraine, rheumatic pains, neuralgia, period pain, toothache and symptoms of colds and influenza.

The features and advantages of the disclosure are more fully shown by the following non-limiting examples, wherein all parts and percentages are by weight, unless otherwise expressly stated.

EXAMPLE 1

An analgesic composition of the disclosure, according to one embodiment thereof, is formulated to include the following ingredients:
 potassium bicarbonate, USP granular
 potassium bicarbonate, USP milled to 250 mesh or smaller particle size powder
 aspirin, USP milled to 325 mesh size
 sweetener, Sucralose™ or Aspartame™ sweetener
 spray dried flavors, oil-free, and pre-dried to less than 0.5% moisture content
 citric acid anhydrous, USP large crystalline size, 10 mesh, pre-dried to less than 0.01% moisture content
 flavoring and taste masking of potassium bicarbonate, vanillin crystals, milled to 150 mesh
 caffeine
 surfactant, sodium laurel sulfate
 carrier resin, polyvinyl pyrollidone (PVP K-30), pre-dried to less than 0.5% moisture content
 alcohol, 99.9% USP grade isopropyl alcohol The foregoing raw materials may be pretreated, with the Sucralose™ sweetener, spray-dried oil-free flavors, vanillin, polyvinyl pyrollidone and citric acid being pre-dried to a moisture content of less than 0.5% by weight, if not already dry to such extent. All material is delumped and screened. Potassium bicarbonate granular and potassium bicarbonate powdered are heat treated to raise pH level thereof to a suitable value, e.g., a pH in a range of 9 to 9.5. The polyvinyl pyrollidone and surfactant are dissolved in a minimum amount of isopropyl alcohol, e.g., utilizing 6 mL of isopropanol per gram of PVP, so that the resulting composition can be introduced into a granulation device to form the granules of the composition. In one embodiment, the Sucralose™ sweetener can be introduced to the polyvinyl pyrollidone and isopropanol to form an additive composition. In other embodiments, surfactant may be added to the polyvinyl pyrollidone and isopropanol, and the resulting composition then may be spray-dried to provide an additive mixture for blending in the formulation.

The machinery used for processing and packaging of the product composition include a twin cone vacuum rotating dryer with a working capacity of 5-10 cubic feet and a bulk density rating of at least 100 pounds per cubic foot. This dryer has a capability of 30 revolutions per hour and a jacket capable of maintaining a temperature of 130° C. A Freewitt or equivalent oscillating granulator is employed, and milling of potassium bicarbonate is carried out using a Co-Mill or a Fitz mill. Additional apparatus for processing the formulation include sealable storage containers, a supply of steam or hot oil, a vacuum pump for drying, a pH meter and scales.

In the granulation operation, a high or low shear granulator/vacuum dryer can be employed, e.g., a granulator/vacuum dryer having a 200 liter working capacity. Alternatively, a closed circuit fluid bed granulator/dryer can be employed, having solvent recovery capability. A peristaltic pump liquid binder delivery system is utilized, with a 10 gallon capacity binder mixing tank and agitator. Hot water for drying is provided at a temperature of approximately 140° F.

Pre-blending operations involved in the manufacturing procedure are carried out with a Twin Cone blender of suitable capacity, e.g. 10 cubic feet working capacity. Final blending is performed with a Twin Cone slant cone blender or a Munson pharmaceutical grade blender of appropriate capacity, e.g., about 80 cubic feet.

The granulation method utilizes aspirin with a particle size of 325 mesh, and heat-treated potassium bicarbonate having a particle size of 250 mesh, as well as surfactant, dried polyvinyl pyrollidone and high purity isopropyl alcohol.

In the granulation process, milled 250 mesh heat treated potassium bicarbonate, 325 mesh aspirin and optionally caffeine are introduced into a high shear Zanchetta mixer.

The polyvinyl pyrollidone and the surfactant are dissolved in the high purity isopropanol to form a binder solution.

During granulation, with choppers and mixing blade set at an appropriate speed, the binder solution containing polyvinyl pyrollidone and surfactant is added completely and the resulting mixture is run until correct size and density of granules is achieved, typically less than 10 minutes. The objective of this granulation operation is to make the granulation particle size as small as possible while achieving maximum density. When the granulation operation is complete, the high shear mixer is set into rotating motion, and heat and vacuum are supplied until granulation particles are dried down to 0.2% or lower moisture content. The dried granulation product then is sized by passage through a Co-Mill to a particle size of 40-60 mesh, and stored in sealed stainless storage bins.

In the final blending operation, the granulation is mixed with flavors, sweetener and heat-treated potassium bicarbonate. Flavors, Sucralose™ sweetener and citric acid granules are delumped and preblended together before final blending. The final product blend contains the preblend granulation and additional heat-treated granules of potassium bicarbonate. The final product blend is introduced to stainless steel, humidity-proof vacuum containers maintained under continuous vacuum.

Packaging is carried out under nitrogen purging, into sealed stick packs, using vertical form/fill/seal stick packaging machines equipped with a nitrogen purge, and conventional box packaging and case packaging equipment.

The amount of aspirin in the final composition product is 650 milligrams, in a ~2 gram dose form (dry solids) for subsequent dissolution in aqueous medium, and the final composition product additionally contains 350 milligrams citric acid in large crystal form, 300-400 milligrams of free-form (non-agglomerate) potassium bicarbonate, and Sucralose™ sweetener, vanillin and flavor ingredients, with a suitable amount of surfactant below 0.1 weight percent, e.g., 0.016 to 0.018 weight percent sodium laurel sulfate, based on the weight of the granules, and polyvinyl pyrollidone being present at a suitable concentration, e.g., in a range of from 1.8 to 2 percent by weight, based on the weight of the granules. In general, the total amount of potassium bicarbonate in the composition, including both granules and free-form, is in a range of from 700 to 1500 mg. The composition may for example contain the aforementioned 300-400 mg of free-form heat-treated potassium bicarbonate, and approximately 700 mg heat-treated potassium bicarbonate in the granules. The formulated product is granulated so that it is non-floating as regards the constituent particles, e.g., in a particle size range of from 40-60 mesh. The flavor ingredients are essentially completely oil-free in character, in order to provide rapid solubilization of the effervescent, potassium-based soluble aspirin composition.

EXAMPLE 2

The ~2 gram dose form soluble aspirin composition of EXAMPLE 1 dissolves in water in less than 30 seconds to constitute a ready to drink dose, when added to 2 ounces of cold water. Upon combination of the dry solids composition with water, a chemical reaction takes place that reacts the aspirin, potassium bicarbonate and citric acid, to yield potassium acetylsalicylate. The potassium acetylsalicylate immediately dissolves in water, leaving no undissolved residue.

While the disclosure has been has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A soluble aspirin composition, comprising: (i) granules including aspirin, heat-treated bicarbonate salt, pharmaceutically-acceptable resin and surfactant, in mixture with: (ii) crystalline particles of pharmaceutically-acceptable acid; and (iii) crystalline particles of heat-treated bicarbonate salt; wherein the soluble aspirin composition when introduced to water undergoes reaction of the crystalline particles of pharmaceutically-acceptable acid with the heat-treated bicarbonate salt and the aspirin to effect effervescing action and disintegration of the granules, with conversion of the aspirin to an acetylsalicylate compound of the bicarbonate salt cation, so that the composition rapidly dissolves in the water, without occurrence of undissolved residue, and wherein the pharmaceutically-acceptable acid comprises citric acid, and the surfactant comprises sodium laurel sulfate.

2. The soluble aspirin composition of claim 1, wherein the bicarbonate salt comprises one or more of potassium bicarbonate, sodium bicarbonate, calcium bicarbonate, magnesium carbonate and lithium carbonate.

3. The soluble aspirin composition of claim 1, wherein aspirin is present at a concentration of from 50 to 2000 mg.

4. The soluble aspirin composition of claim 1, wherein the heat-treated bicarbonate salt comprises heat-treated potassium bicarbonate having a pH in a range of from 8.4 to 10.

5. The soluble aspirin composition of claim 1, wherein the pharmaceutically-acceptable resin is selected from the group consisting of polyvinyl pyrollidone, polyvinyl alcohol, acrylic acid polymers, methacrylic acid polymers, sulfonated styrenes, sulfonated dimethyl benzenes, modified celluloses, and dextrans.

6. The soluble aspirin composition of claim 1, wherein the pharmaceutically-acceptable resin comprises polyvinyl pyrollidone.

7. The soluble aspirin composition of claim 1, wherein the pharmaceutically-acceptable resin has a concentration in a range of from about 1.5 to about 4 percent by weight, based on total weight of the granules.

8. The soluble aspirin composition of claim 1, wherein the surfactant has a concentration in a range of from 0.01 to 0.1 weight percent, based on total weight of the granules.

9. The soluble aspirin composition of claim 1, further comprising at least one ingredient selected from the group consisting of flavorants, sweeteners, acetaminophen and caffeine.

10. The soluble aspirin composition of claim 1, oil-free in character, and having a moisture content less than 0.5% by weight, based on total weight of the composition.

11. A dry solids aspirin composition, comprising: (i) granules including aspirin, heat-treated potassium bicarbonate, pharmaceutically-acceptable resin and surfactant, in mixture with: (ii) crystalline particles of pharmaceutically-acceptable acid; and (iii) crystalline particles of heat-treated potassium bicarbonate, wherein the pharmaceutically-acceptable acid comprises citric acid, and the surfactant comprises sodium laurel sulfate.

12. The dry solids aspirin composition of claim 11, wherein aspirin is present at a concentration of from 50 to 2000 mg.

13. The dry solids aspirin composition of claim 11, wherein pH of the heat-treated potassium bicarbonate is in a range of from 8.4 to 10.

14. The dry solids aspirin composition of claim 12, wherein the pharmaceutically-acceptable resin comprises polyvinyl pyrollidone.

15. The dry solids aspirin composition of claim 14, wherein the pharmaceutically-acceptable resin has a concentration in a range of from about 1.5 to about 4 percent by weight, based on total weight of the granules.

16. The dry solids aspirin composition of claim 11, further comprising at least one ingredient selected from the group consisting of flavorants, sweeteners, acetaminophen and caffeine.

17. The dry solids aspirin composition of claim 11, oil-free in character, and having a moisture content less than 0.5% by weight, based on total weight of the composition.

18. A method of making a soluble aspirin composition, comprising: agglomerating powdered aspirin and powdered heat-treated bicarbonate salt with a pharmaceutically-acceptable resin and surfactant, to form granules; and mixing the granules with crystalline particles of pharmaceutically-acceptable acid and crystalline particles of heat- treated bicarbonate salt, to yield the soluble aspirin analgesic composition, wherein the pharmaceutically-acceptable acid comprises citric acid, and the surfactant comprises sodium laurel sulfate.

19. A method of providing aspirin treatment to a subject in need thereof, comprising mixing an effective amount of the dry solids aspirin composition of claim 11 with a solubilizing quantity of aqueous medium, to produce a solubilized aspirin solution, and administering said solubilized aspirin solution to said subject.

20. The method of claim 19, wherein said aqueous medium comprises water.

21. The method of claim 19, wherein said aspirin treatment comprises treatment of one or more of headache, migraine, rheumatic pains, neuralgia, menstrual pain, toothache, and symptoms of colds and influenza.

* * * * *